United States Patent
Schryvers et al.

(10) Patent No.: US 6,211,343 B1
(45) Date of Patent: Apr. 3, 2001

(54) LACTOFERRIN RECEPTOR PROTEIN

(75) Inventors: Anthony B. Schryvers; Robert A. Bonnah, both of Calgary (CA)

(73) Assignee: Connaught Laboratories Limited, Toronto (CA)

( * ) Notice: Subject to any disclaimer, the term of this patent is extended or adjusted under 35 U.S.C. 154(b) by 0 days.

(21) Appl. No.: 09/370,869

(22) Filed: Aug. 10, 1999

Related U.S. Application Data

(62) Division of application No. 08/552,232, filed on Nov. 2, 1995, now Pat. No. 6,048,539.

(51) Int. Cl.[7] .................................................. C08H 1/00
(52) U.S. Cl. ..................... 530/412; 530/413; 530/350; 424/249.1; 424/250.1
(58) Field of Search .................................. 530/350, 412, 530/413; 424/249.1, 250.1, 253.1, 251.1

(56) References Cited

U.S. PATENT DOCUMENTS 5,141,743 * 8/1992 Schryvers .

OTHER PUBLICATIONS

Schryvers et al. Infection&Immunity. May 1988. 56(5): 1144–1149.*

Menozzi et al. Infection&Immunity. Nov. 1991. 59(11): 3982–3988.*

Dyer et al. Infection&Immunity. Apr. 1988. 56(4): 977–983.*

* cited by examiner

Primary Examiner—Jennifer Graser
(74) Attorney, Agent, or Firm—Sim & McBurney

(57) ABSTRACT

An isolated and purified lactoferrin receptor protein is isolated and purified from bacterial pathogens, including Moraxella and Neisseria, and has a molecular weight of between about 70,000 and about 90,000, as determined by SDS-PAGE. Such lactoferrin receptor protein may be provided in combination with a lactoferrin receptor protein from the bacterial pathogen of a molecular weight of about 100,000 to about 105,000 daltons. The lactoferrin receptor protein may be produced by providing a solubilized membrane preparation from the bacterial pathogen containing lactoferrin receptor proteins, non-lactoferrin receptor proteins and other contaminants, complexing the lactoferrin receptor proteins with lactoferrin and purifying the resulting complexes substantially free from the non-lactoferrin receptor proteins and the other contaminants, and separating the novel lactoferrin receptor protein from the complexes. The lactoferrin receptor protein is useful in diagnostic applications and immunogenic compositions, particularly for in vivo administration to a host to confer protection against disease caused by a bacterial pathogen that produces the lactoferrin receptor protein or produces a protein capable of inducing antibodies in a host specifically reactive with the lactoferrin receptor protein.

6 Claims, 1 Drawing Sheet

LACTOFERRIN RECEPTOR PROTEIN

This application is a division of application Ser. No. 08/552,232 filed Nov. 2, 1995 (now U.S. Pat. No. 6,048, 539).

FIELD OF THE INVENTION

The present invention relates to the field of immunology and is particularly concerned with a novel lactoferrin receptor protein isolated and purified from bacterial pathogens and methods of production, and uses thereof.

BACKGROUND TO THE INVENTION

Most living organisms require a continuous supply of iron to maintain growth and thus have evolved efficient mechanisms for acquisition of iron under conditions of limitation (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure) A common mechanism found in many bacterial species involves the synthesis and secretion of small iron-chelating molecules, siderophores, which complex with iron and are subsequently bound and internalized via specific receptors at the bacterial surface (ref. 2). This mechanism is effective in a wide variety of environments and is often found in bacterial species that are present in a variety of ecological niches.

The vertebrate host provides an iron-restricted environment to potential bacterial pathogens, largely due to the sequestration of extracellular iron by the host iron-binding glycoproteins, namely transferrin (Tf) and lactoferrin (Lf). Although a siderophore-mediated mechanism should be effective in this setting, some bacterial species have evolved alternative mechanisms of iron acquisition that are adapted to their particular host. Thus, some members of the Pasteurellaceae and Neisseriaceae are capable of specifically binding and effectively acquiring iron from the host Tf and in some cases, Lf. This is mediated by receptors present at the bacterial surface whose expression is induced by restricting the level of available iron in the medium.

Receptors that are specific for Tf from the host (ref. 3) have been identified in a variety of important human and veterinary pathogens as well as some commensal species (Table 1). To date, Tf receptors have only been identified in bacterial species within the Pasteurellaceae and Neisseriaceae. In most species the Tf receptor has been shown to consist of two proteins, Tf-binding protein I (Tbp1) and Tf-binding protein 2 (Tbp2). The genes encoding these proteins have been cloned from *Neisseria meningitidis* (ref. 13), *N. gonorrhoeae* (refs. 14 and 15), *Haemophilus influenzae* (ref. 16) and *Actinobacillus pleuropneumoniae* (refs. 17 and 18). The predicted amino acid sequences of Tbp2 proteins reveal homology to the lipoprotein signal peptidase recognition site suggesting that it is lipid-modified and retains an association with the outer membrane via its lipid tail. Lipidation of Tbp2 has been confirmed by labelling (refs. 13 and 19) and evidence is accumulating that Tbp2 is largely surface exposed (refs. 20 and 21). Isogenic mutants deficient in the production of Tbp2 demonstrate severely limited ability to utilize transferrin as a sole iron source during in vitro growth studies, suggesting Tbp2 plays an important, albeit not essential role in iron acquisition (refs. 14, 16, 22).

Based on its homology with other TonB-dependant outer membrane proteins Tbp1 receptor proteins are believed to have several regions which span the outer membrane (ref. 23) (see ref. 35 for a topological model that can be applied to Tbp1). Similarly, based on the results obtained with the FepA receptor (ref. 25), Tbp1 is thought to act as a gated pore which allows the passage of iron from the transferrin and lactoferrin molecules, which are themselves not internalized, to the periplasm where it is bound by the ferric iron-binding protein, FbpA. Two additional proteins FbpB and FbpC are believed to be involved in the transport of iron across the cytoplasmic membrane.

The transport of iron across the outer membrane is believed to occur in a TonB-dependent manner, in that amino acid sequences referred as the "TonB box", located in a number of TonB-dependent outer membrane receptor proteins have also been identified in Tbp1. The inability to utilize human transferrin following insertional inactivation of the *H. influenzae* TonB homologue clearly supports this theory. In addition, mutants in which the Tbp1 protein has been insertionally inactivated are unable to utilize transferrin as a sole iron source, supporting its essential role in iron acquisition from transferrin.

Bacterial lactoferrin receptors have only been described for human pathogens in the Neisseriaceae, and were thought to consist of a single protein, Lbp1. Amino acid sequence analysis of the Lbp1 protein shows high homology to Tbp1 (refs. 26, 35, 36), and isogenic mutant analysis deficient in Lbp1 suggests an essential role of Lbp1 in iron acquisition (refs. 24 and 28). Recent genetic evidence suggests that similar to the tbpBA operonic organization, an open reading frame is located immediately upstream of the lbpA structural gene which may encode a Tbp2 homologue, Lbp2 (ref. 35).

Properties of lactoferrin receptor proteins of bacterial pathogens indicate that these proteins have utility in diagnosis of and vaccination against diseases caused by such bacterial pathogens that produce lactoferrin receptor proteins or proteins capable of raising antibodies specifically reactive with lactoferrin receptor proteins.

It would be advantageous to provide purified lactoferrin receptor proteins (and methods of purification thereof) for use as antigens, immunogenic preparations, including vaccines, carriers for other antigens and immunogens and the generation of diagnostic reagents.

SUMMARY OF THE INVENTION

The present invention is directed towards the provision of purified and isolated lactoferrin receptor protein from a bacterial pathogen having a molecular mass of about 70,000 and about 90,000 daltons wherein the molecular mass is determined by sodium dodecyl sulphate polyacrylamide gel electrophoresis (SDS-PAGE).

In accordance with one aspect of the invention, there is provided a lactoferrin receptor protein isolated and purified from a bacterial pathogen and having an apparent molecular mass of about 70,000 to about 90,000 daltons as determined by SDS-PAGE.

The bacterial pathogens from which the lactoferrin receptor protein may be isolated and purified include *Neisseria meningitidis, Neisseria gonorrhoeae, Moraxella catarrhalis, Moraxella bovis* and *Moraxella lacunata*. The about 70 to about 90 kDa lactoferrin receptor protein is at least about 70 wt % pure, preferably at least about 90 wt % pure, and may be in the form of an aqueous solution thereof.

The lactoferrin receptor protein, sometimes referred to herein by the designation "Lbp2", may be provided in a form substantially free from a lactoferrin receptor protein having a molecular weight of about 100,000 to about 105,000 daltons, as determined by SDS-PAGE, sometimes referred to herein by the designation "Lbp1".

Alternatively, the novel lactoferrin receptor protein provided herein may comprise a mixture of the lactoferrin receptor proteins. In another aspect of the present invention, therefore, there is provided a composition comprising a first lactoferrin receptor protein (Lbp1) having a molecular weight of about 100,000 to about 105,000 and a second lactoferrin receptor protein having a molecular weight of between about 70,000 and about 90,000 daltons, wherein the molecular weights are determined by SDS-PAGE and the lactoferrin receptor proteins are isolated and purified from a bacterial pathogen, which may be any of the pathogens mentioned above.

Such composition may be at least about 70% pure by weight, preferably at least about 90% pure by weight. Such composition also may be provided substantially free from transferrin receptor proteins of the pathogen.

The present invention also provides an immunogenic composition comprising an immunoeffective amount of an active component, which may be the novel lactoferrin receptor protein, provided herein alone or together with Lbp1 along with a pharmaceutically acceptable carrier therefor. The immunogenic composition may be formulated as a vaccine for in vivo administration to a host to confer protection against diseases caused by a bacterial pathogen which produces a lactoferrin receptor protein having a molecular weight of about 70,000 to about 90,000 daltons, or that produces a protein capable of inducing antibodies in the host specifically reactive with the lactoferrin receptor protein. The immunogenic composition may be formulated as a microparticle capsule, ISCOM or liposome preparation. The immunogenic composition may be used in combination with a targeting molecule for delivery to specific cells of the immune system or to mucosal surfaces. Some targeting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, Quil A, calcium phosphate, calcium hydroxide, zinc hydroxide, a glycolipid analog, an octadecyl ester of an amino acid, a muramyl dipeptide and a lipoprotein. Advantageous combinations of adjuvants are described in copending U.S. patent application Ser. No. 08/261,194 filed Jun. 16, 1994, assigned to the assignee hereof and the disclosure of which is incorporated herein by reference. The immunogenic composition may be substantially free from transferrin receptor protein of the pathogen.

The invention further includes an antibody specific for the novel lactoferrin receptor protein provided herein producible by immunizing a host with an immunogenic composition as provided herein.

In a further aspect of the invention, there is provided a method of generating an immune response in a host, comprising administering thereto an immuno-effective amount of the immunogenic composition as provided herein. The immune response may be a humoral or a cell-mediated immune response. Hosts in which protection against disease may be conferred include primates including humans.

The immune response which is generated may provide protection to the host against disease caused by a bacterial pathogen that produces a lactoferrin receptor protein having a molecular weight of between about 70,000 and about 90,000 daltons or that produces a protein capable of inducing antibodies in the host specifically reactive with the lactoferrin receptor protein.

The present invention provides, in an additional aspect thereof, a method for producing a vaccine comprising administering the immunogenic composition provided herein to a test host to determine an amount and a frequency of administration of the lactoferrin receptor protein to confer protection against disease caused by a bacterial pathogen that produces the lactoferrin receptor protein having a molecular weight between about 70,000 and about 90,000 or a protein capable of inducing antibodies in a host specifically reactive with the lactoferrin receptor protein; and formulating the lactoferrin receptor protein in a form suitable for administration to a treated host in accordance with said determined amount and frequency of administration. The treated host may be a human.

A further aspect of the invention provides a method of determining the presence in a sample, of antibodies specifically reactive with a lactoferrin receptor protein of a bacterial pathogen having a molecular weight of between about 70,000 and about 90,000 daltons, comprising the steps of:

(a) contacting the sample with the lactoferrin receptor protein as provided herein to produce complexes comprising the lactoferrin receptor protein and any said antibodies present in the sample specifically reactive therewith; and (b) determining production of the complexes.

In a further aspect of the invention, there is provided a method of determining the presence, in a sample, of a lactoferrin receptor protein of a bacterial pathogen and having a molecular weight of between about 70,000 and about 90,000 daltons, comprising the steps of:

(a) immunizing a subject with the lactoferrin receptor protein as provided herein, to produce antibodies specific for the lactoferrin receptor protein;

(b) contacting the sample with the antibodies to produce complexes comprising any outer membrane protein present in the sample and said outer membrane protein specific antibodies; and (c) determining production of the complexes.

A further aspect of the invention provides a diagnostic kit for determining the presence of antibodies in a sample specifically reactive with the lactoferrin receptor protein of a bacterial pathogen and having a molecular weight of between about 70,000 and about 90,000 daltons, comprising:

(a) the lactoferrin receptor protein as provided herein;

(b) means for contacting the lactoferrin receptor protein with the sample to produce complexes comprising the lactoferrin receptor protein and any said antibodies present in the sample; and (c) means for determining production of the complexes.

The invention also provides a diagnostic kit for detecting the presence, in a sample, of a lactoferrin receptor protein of a bacterial pathogen and having a molecular weight of between about 70,000 and about 90,000, comprising:

(a) an antibody specific for the novel lactoferrin receptor protein as provided herein;

(b) means for contacting the antibody with the sample to produce a complex comprising the lactoferrin receptor protein and lactoferrin receptor protein-specific antibody; and (c) means for determining production of the complex.

In an additional aspect, the present invention provides a method of producing a vaccine, comprising administering the immunogenic composition provided herein to a test host to determine an amount and a frequency of administration to confer protection against disease caused by a bacterial pathogen that produces a lactoferrin receptor protein having a molecular weight of between about 70,000 and about 90,000 daltons or a protein capable of inducing antibodies in a test host specifically reactive with the lactoferrin receptor protein; and formulating the immunogenic composition in a form suitable for administration to a treated host, which may be a human, in accordance with the determined amount and frequency of administration.

The present invention additionally provides a method of producing antibodies specific for a lactoferrin receptor protein having a molecular weight of between about 70,000 and about 90,000 daltons, comprising:

(a) administering the lactoferrin receptor protein provided herein to at least one mouse to produce at least one immunized mouse;

(b) removing B-lymphocytes from the at least one immunized mouse;

(c) fusing the B-lymphocytes from the at least one immunized mouse with myeloma cells, thereby producing hybridomas;

(d) cloning the hybridomas;

(e) selecting clones which produce anti-lactoferrin receptor protein antibody;

(f) culturing the anti-lactoferrin receptor protein antibody-producing clones; and then (g) isolating anti-lactoferrin receptor protein antibodies from the cultures.

The present invention further includes procedures for isolating and purifying the novel lactoferrin receptor protein from a bacterial pathogen, either in a form free from Lbp1 or in a form of a purified mixture with Lbp1.

Accordingly, in another aspect of the invention, there is provided a method of producing a lactoferrin receptor protein from a bacterial pathogen, comprising the steps of:

(a) providing a solubilized membrane preparation from the bacterial pathogen containing lactoferrin receptor proteins, non-lactoferrin receptor proteins and other contaminants, (b) complexing the lactoferrin receptor proteins with lactoferrin and purifying the resulting complexes substantially free from non-lactoferrin receptor proteins and the other contaminants, and (c) separating from the complexes a lactoferrin receptor protein having a molecular weight of between about 70,000 and about 90,000 daltons.

This isolation and purification procedure may be carried out in any desired manner. The lactoferrin receptor proteins may further comprise a second lactoferrin receptor protein having a molecular weight of about 100,000 to about 105,000 daltons (i.e. lbp1).

In one embodiment, step (b) is effected by complexing the two lactoferrin receptor proteins with lactoferrin and separating the complexes from the membrane preparation, and step (c) produces a purified mixture of the two lactoferrin receptor proteins.

In another embodiment, the non-lactoferric receptor protein include transferrin receptor proteins of the pathogen, step (b) is effected by removing the second lactoferrin receptor protein (Lbp1) and the transferrin receptor proteins (Tbp1 and Tbp2) from the solubilized membrane preparation to provide a depleted membrane preparation, complexing the first-mentioned lactoferrin receptor protein with lactoferrin in the depleted membrane preparation and removing the complex so formed from the depleted membrane preparation.

In forming the complexes with the transferrin receptor protein(s), the transferrin may be coupled to a carrier molecule, which may be a Sepharose, such as cyanogen bromide activated CH-Sepharose. In one embodiment, the lactoferrin may be conjugated to biotin and the Sepharose in streptavidin-Sepharose to couple the lactoferrin to streptavidin.

In this application, the term "lactoferrin receptor protein" is used to define a family of lactoferrin receptor proteins of a variety of pathogens having a molecular mass of between about 70,000 and 90 daltons and includes proteins having variations in their amino acid sequences including those naturally occurring in various strains of bacterial pathogens. In this application, a first protein or peptide is a "functional analog" of a second protein or peptide if the first protein is immunologically related to and/or has the same function as the second protein or peptide. The functional analog may be, for example, a fragment of the protein or a substitution, addition or deletion mutant thereof. The invention also extends to such functional analogs.

Advantages of the present invention include:

a method for isolating purified about 70,000 to about 90,000 daltons lactoferrin receptor protein of a bacterial pathogen that produces the lactoferrin receptor protein;

an isolated and purified lactoferrin receptor protein of a bacterial pathogen having a molecular weight of about 70,000 to about 90,000 daltons as determined by SDS-PAGE; and diagnostic kits and immunological reagents for specific identification of bacterial pathogens and hosts infected thereby.

BRIEF DESCRIPTION OF THE FIGURES

The present invention will be further understood from the following description with reference to the Figures, in which.

GENERAL DESCRIPTION OF INVENTION

Figure 1:
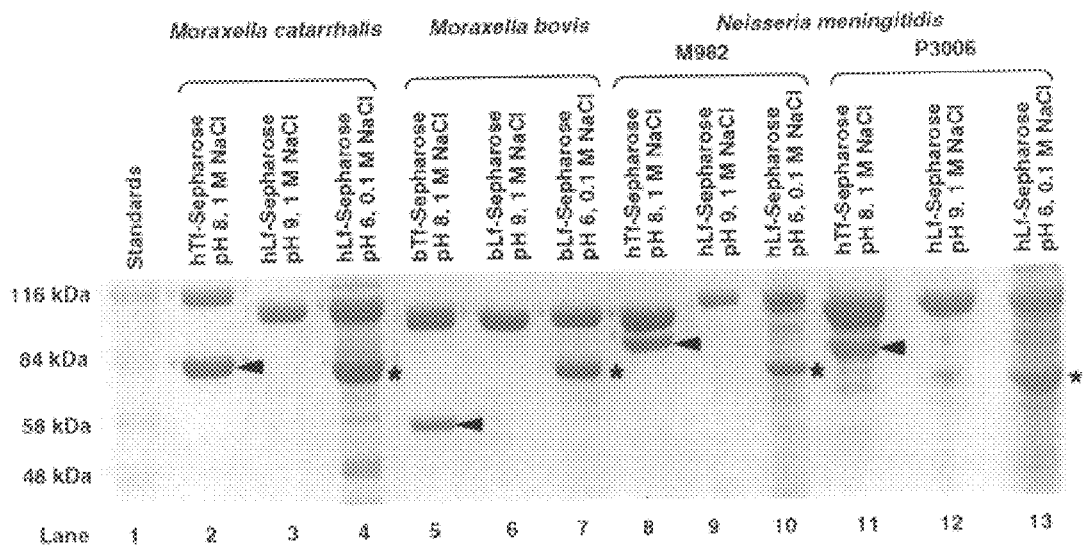
FIG. 1 shows an SDS-PAGE analysis of transferrin isolated binding proteins and lactoferrin binding proteins isolated from bacterial pathogens.

The present invention provides a novel lactoferrin receptor protein which is isolated and purified from a pathogen and has a molecular weight of between 70,000 and 90,000 daltons as determined by SDS-PAGE and herein referred to sometime as Lbp2. There is some heterogenicity in size among the Lbp2 protein from different species, as seen in FIG. 1. The novel Lbp2 protein may be isolated from a variety of bacterial pathogens, including *Neisseria*

*meningitidis, Neisseria gonorrhoeae, Moraxella catarrhalis, Moraxella bovis* and *Moraxella lacunata*.

The Lbp2 protein may be isolated using affinity purification procedures. In U.S. Pat. No. 5,141,743, there is described an affinity purification procedure which results in the isolation of two transferrin receptor proteins, Tbp1 and Tbp2, from a variety of bacterial pathogens, including Moraxella catarrhalis (FIG. 1, lane 2), *Neisseria meningitidis* (lanes 8, 11) and *M. bovis* (lane 5). Using conditions selected to minimize isolation of contaminating proteins, a single host-specific lactoferrin receptor protein, Lbp1, is isolated from the same species and strains (lanes 3, 6, 9 and 12).

Such affinity purification procedure is effected using transferrin or lactoferrin, as the case may be, which normally is complexed to a suitable matrix material, such as Sepharose, for example, though linkage via cyanogen bromide activated CH-Sepharose or biotin-LC-hydrazide, which is subsequently joined to Streptavidin Sepharose. The transferrin- or lactoferrin-matrix conjugate is contacted with a solubilized membrane preparation from the bacterial pathogen, following removal of soluble material, under pH and salt conditions, generally high levels of salt and pH, which causes the receptor protein to define the transferrin or lactoferrin, as the case may be. The resulting solid complexes are separated from the liquid phase and the respective proteins may be recovered by elution of the solid complexes with a gradient of chaotropic agents, such as guanidine hydrochloride.

To obtain the Lbp2 alone from the solubilized membrane preparation, the Lbp1 and transferrin receptor proteins first are removed and the incubation with the lactoferrin-matrix conjugate is repeated under low salt and pH conditions, resulting in solid complex formation. Following removal of the solid complexes, the Lbp2 protein can be removed by elution from the solid complex.

To obtain from the solubilized membrane preparation the Lbpt2 in admixture with Lbpt1, the solubilized membrane preparation may be contacted with the transferrin-matrix conjugate under the high salt and pH conditions favouring non-binding the Lbpt2 and then separating the solid complexes formed, thereby separating the Lbpt1 and Lbpt2 proteins from the transferrin receptor proteins.

Figures 3, 4:
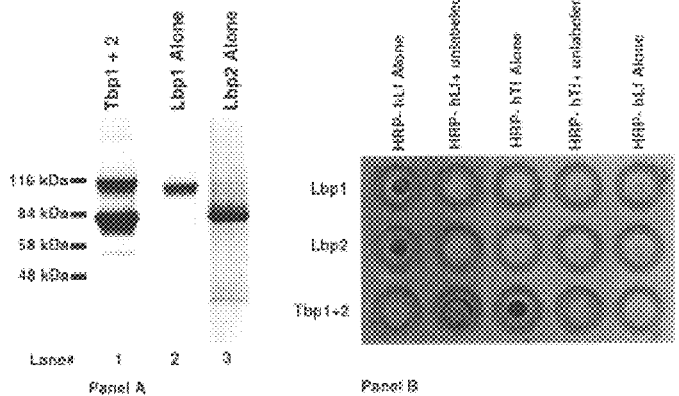
FIG. 3 shows an SDS-PAGE analysis of lactoferrin binding proteins Lbp1 and Lbp2 isolated from *Moraxella catarrhalis*.
FIG. 4 shows the specificity of transferrin binding protein for binding transferrin and lactoferrin binding protein for binding lactoferrin.

Following affinity isolation of Tbp1+2, Lbp1 and Lbp1+2, the samples were subjected to SDS-PAGE and were subsequently electroblotted and analyzed for reactivity against various antisera, as seen in FIG. 3. Following affinity isolation of Lbp2, the purified preparations were immobilized on a nitrocellulose membrane and tested for binding activity in the solid-phase binding assay (FIG. 3).

In additional embodiments of the present invention, the Lbp2 protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus* and *Pseudomonas aeruginosa*. Particular antigens which can be conjugated to Lbp2 protein and methods to achieve such conjugations are described in published PCT application WO 94/12641, the disclosure of which is hereby incorporated by reference thereto.

In another embodiment, the carrier function of Lbp2 protein may be used, for example, to induce immunity toward abnormal polysaccharides of tumor cells, or to produce anti-tumor antibodies that can be conjugated to chemotherapeutic or bioactive agents.

The invention extends to lactoferrin binding proteins as provided herein for use as an active pharmaceutical substance, particularly as an active ingredient in a vaccine against disease caused by infection with a pathogen.

It is clearly apparent to one skilled in the art, that the various embodiments of the present invention have many applications in the fields of vaccination, diagnosis, treatment of bacterial infections and the generation of immunological reagents. A further non-limiting discussion of such uses is further presented below.

1. Vaccine Preparation and Use

Immunogenic compositions, suitable to be used as vaccines, may be prepared from the lactoferrin receptor protein, as well as analogs and fragments thereof, as disclosed herein. The vaccine elicits an immune response which produces antibodies, including anti-lactoferrin receptor antibodies and antibodies that are opsonizing or bactericidal. Should the vaccinated subject be challenged by a bacterial pathogen that produce a lactoferrin receptor protein having a molecular weight of between about 70,000 and about 90,000 daltons, the antibodies bind to the lactoferrin receptor and thereby prevent access of the bacterial pathogen to an iron source which is required for viability. Furthermore, opsonizing or bactericidal anti-lactoferrin receptor protein antibodies may also provide protection by alternative mechanisms.

Immunogenic compositions including vaccines may be prepared as injectables, as liquid solutions or emulsions. The lactoferrin receptor protein may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the lactoferrin receptor protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the lactoferrin receptor protein. Suitable regimes for initial administration and booster doses are also variable, but may include an initial administration followed by subsequent administrations. The dosage may also depend on the route of administration and will vary according to the size of the host.

The concentration of the lactoferrin receptor protein Lbp2, with or without the corresponding Lbp1, in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens. In particular applications, it may be desirable to provide mixtures comprising immunologically distinct lactoferrin binding proteins, including immunologically-distinct Lbp2.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4, 855,283 and ref. 29) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 30), reported that octadecyl esters of aromatic amino acids complexed with a recombinant hepatitis B surface antigen, enhanced the host immune responses against hepatitis B virus.

2. Immunoassays

The lactoferrin receptor protein of the present invention is useful as an immunogen for the generation of anti-lactoferrin receptor protein antibodies, as an antigen in immunoassays including enzyme-linked immunosorbent assays (ELISA), RIAs and other non-enzyme linked antibody binding assays or procedures known in the art for the detection of anti-bacterial and anti-Lbp2 antibodies. In ELISA assays, the lactoferrin receptor protein is immobilized onto a selected surface, for example, a surface capable of binding proteins such as the wells of a polystyrene microtiter plate. After washing to remove incompletely adsorbed lactoferrin receptor protein, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound lactoferrin receptor protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the growth of bacteria.

Neisseria and Moraxella species cells were propagated in liquid Brain Heart Infusion broth (BHI; Gibco Laboratories). *Neisseria meningitidis* M982 and M986 were obtained from Dr. E. Mackie and Dr. C. E. Frasch, (FDA, Bethesda), whereas P3006, used for PCR amplification of the C-terminal region of the *N. meningitidis* lbpB gene region, was obtained from Dr. Jan Poolman (University of Amsterdam). The *Moraxella catarrhalis* and *M. bovis* isolates used for these studies have been described previously (refs. 31 and 32).

For binding and affinity isolation experiments, iron-restriction of bacterial cells was performed as described previously. Growth studies were performed using plate assays in which iron sources were applied to Brain Heart Infusion (Gibco) agar plates containing 100 μM Etheylenediamminedi(o-hydroxyphenyllacetic) acid (BHI+ EDDA) on which a suspension of iron-limited cells had previously been spread (ref. 34). 200 μg of each iron-saturated transferrin or lactoferrin was applied onto the sterile disks prior to application to the plates. The plates were examined after 24 and 48 hours of incubation for cell growth surrounding the disks containing the various iron sources.

Example 2

This Example describes the ability of selected bacterial pathogens to utilize various iron sources.

Iron saturated bacteria were spread onto BHI plates containing EDDA (100 μM) as described above and discs containing human transferrin (hTf), bovine transferrin (bTf), human lactoferrin (hLf) and bovine lactoferrin (bLf). Human lactoferrin and transferrin, and bovine transferrin used for the binding and growth studies was obtained from Sigma, USA. Bovine lactoferrin was obtained from Serva, USA. The bacteria tested were *N. meningitidis* a human pathogen; *N. meningitidis* lbpA::Gm which is deficient in lactoferrin binding protein; *N. meningitidis* tbpA::Kan which is deficient in transferrin binding protein; *M. catarrhalis* (a human pathogen) and *M. bovis* (a bovine pathogen). Growth surrounding the disk impregnated with the iron source was the measure of the ability of the various bacteria to utilize the iron source. The results are shown in Table 2 and indicate that:

(a) each of the pathogens could utilize transferrin or lactoferrin as the source of iron and thus express transferrin and lactoferrin receptor proteins;

(b) the human pathogen (*N. meningitidis* and *M. catarrhalis*) were only able to utilize human transferrin and human lactoferrin;

(c) the bovine pathogen (*M. catarrhalis*) was only able to utilize bovine transferrin and bovine lactoferrin; and (d) deletion of the genes encoding transferrin receptor protein (Tbp1) and lactoferrin receptor protein (Lbp1) from *N. meningitidis* prevented the utilization of transferrin and lactoferrin respectively.

Example 3

This Example describes the preparation of biotin-LC-hydrazide-lactoferrin derivatives.

Covalent linkage of biotin to lactoferrin was achieved using biotin-LC-hydrazide which can be used to couple biotin to carbohydrate groups following mild periodate oxidation. Equal volumes of ice cold human lactoferrin (2 mg/ml) and 20 mM sodium periodate dissolved in 0.1 M sodium acetate buffer (pH 5.5) to a concentration of 2 mg/ml were added together and allowed to react on ice in the dark for 20 minutes. Glycerol was subsequently added to a final concentration of 15 mM to quench the reaction, and the sample was dialyzed overnight against acetate buffer. Biotin-LC-Hydrazide dissolved in DMSO was added to the dialyzed samples to a final concentration of 5 mM, and the mixture was incubated at room temperature for two hours with mild agitation, then dialyzed against 20 mM Tris buffer, pH 8.

Example 4

This Example describes the isolation and characterization of transferrin receptor protein 1 (Tbp1), transferrin receptor protein 2 (Tbp2), lactoferrin receptor protein (Lbp1) and lactoferrin receptor protein 2 (Lbp2), by affinity isolation.

Transferrin receptor proteins Tbp1 and Tbp2 and lactoferrin receptor protein Lbp1 have been affinity isolated previously as described above and U.S. Pat. No. 5,141,743 which is incorporated herein by reference thereto and ref. 34. Transferrin-Sepharose and lactoferrin-Sepharose columns were prepared from the transferrin and lactoferrin preparations by coupling a 10 mg/ml solution of transferrin or lactoferrin to activated Sepharose (Pharmacia, Uppsala, Sweden) according to the manufacturer's instruction for coupling ligands to cyanogenbromide-activated Sepharose (CNBr-Sepharose). The resulting column was washed with 2 column volumes of 50 mM Tris buffer (pH 8.0) containing 6 M guanidine hydrochloride to remove non-covalently bound transferrin or lactoferrin.

Bacterial cells resuspended from fresh cultures on chocolate plates were used to inoculate prewarmed Brain Heart Infusion broth containing 100 $\mu$M EDDA (ethylenediamindi(O-hydroxyphenyl)acetic acid) to a starting $A_{600}$ of 0.02. The resulting culture was incubated at 37° C. with shaking for 16 hours prior to harvest by centrifugation at 9,000×g for 15 minutes. The cells were resuspended to 0.2 gm/ml in 50 mM TrisHCl, pH 8 buffer containing 50 $\mu$g/ml phenylmethylsulfonyl fluoride. The cells were lysed by passing the suspension through a French pressure cell at 16,000 lb/in$_2$ and cell debris was removed by centrifugation at 9,000×g for 15 minutes. Crude total membranes were collected by centrifugation at 140,000×g for 1 hour and resuspended in 50 mM TrisHCl, pH 8 buffer.

Ten mg of crude membrane protein was diluted in 1 ml of 50 mM Tris-HCl, 1 M NaCl, 20 mM EDTA (pH 8.0) buffer containing 0.75% Sarkosyl NL37. The solubilized membrane preparation was centrifuged at 10,000 rpm for 10 minutes to remove cell debris. The supernatant containing outer membrane components was mixed with 100 $\mu$l of the transferrin-Sepharose resin or lactoferrin-Sepharose resin and incubated for 1 hour to allow the binding of transferrin receptor protein or lactoferrin receptor protein to its respective ligand. The resin was collected by centrifugation at 500×g for 10 minutes and resuspended in 50 mM TrisHCl, 1 M NaCl, 10 mM EDTA, 0.75% "SARKOSYL", pH 8 buffer. The resin was again collected by centrifugation and washed two more times in the above buffer. After the final wash, the resin was resuspended in 20 mls of the above buffer and poured into 1 cm diameter chromatography column. The packed resin was washed with an additional 10 mls of 50 mM TrisHCl, 1 M NaCl, 10 mM EDTA, 0.5% "SARKOSYL" and the receptor proteins were eluted by application of a 60 ml gradient of 1 to 3 M guanidine hydrochloride in 50 mM TrisHCl, 1 M NaCl, 10 mM EDTA, 0.05% "SARKOSYL". The fractions containing receptor proteins were pooled and dialyzed against two changes of 3 litres of 50 mM TrisHCl, pH 7.5 buffer and one change of phosphate buffered saline (50 mM sodium phosphate, 150 mM NaCl, pH 7.4) and concentrated by ultrafiltration. These previously developed affinity methods result in the isolation of two human transferrin-specific receptor proteins, Tbp1 and Tbp2, from a variety of species including the human pathogens *Moraxella catarrhalis* (FIG. 1, lane 2), and *Neisseria meningitides* (strain M982, lane 8; strain P3006, lane 11). Similarly, two bovine-specific transferrin receptor proteins are isolated from the bovine pathogen, *M. bovis* (lane 5). Using these conditions (originally selected to minimize isolation of contaminating proteins) a single host-specific lactoferrin receptor protein (lanes 3, 6, 9 and 12) is isolated from these same species and strains.

For the isolation of mixtures comprising a first lactoferrin receptor protein having a molecular weight of about 100,000 to about 105,000 daltons (Lbp1) and a second lactoferrin receptor protein having a molecular weight of between about 70,000 and about 90,000 (Lbp2) modifications were made to these affinity isolation procedures. Thus, total membranes of iron-starved *M. catarrhalis*, *M. bovis* and *N. meningitidis* were diluted to a protein concentration of approximately 10 mg/ml and solubilized in 50 mM Tris pH 6 buffer containing 10 mM Etheylenediaminetetraacetic acid (EDTA), 0.6% Sarkosyl and 0.76 M NaCl, then insoluble matter was removed by centrifugation. To achieve affinity isolation of Lbp 1+2, the sample was diluted tenfold with 50 mm Tris buffer pH 6, and incubated in the presence of human lactoferrin covalently coupled to CNBr-activated CH-Sepharose or biotin-LC-hydrazide, for 2 hours at room temperature. For the human lactoferrin-biotin-LC-hydrazide conjugate, the sample was subsequently incubated in the presence of Streptavidin-Sepharose for an additional hour. For analytical purposes, after centrifugation, the pellets were washed three times with pH 6, 50 MM Tris buffer containing 0.1 M NaCl, then resuspended in a small volume of Laemmli sample buffer, and boiled for 5 minutes prior to subjecting the samples to SDS-PAGE, using a 10% acrylamide gel. This modified lactoferrin receptor protein affinity isolation procedure resulted in isolation of a second major protein from *M. catarrhalis* (FIG. 1, lane 4), *M. bovis* (FIG. 1, lane 7) and *N. meningitidis* (strain M982, FIG. 1, lane 10; strain P3006, FIG. 1, lane 13). This protein has a molecular weight of between about 70,000 and 90,000 and is shown by an asterisk in FIG. 1. This lactoferrin receptor protein is herein referred to as binding Lbp2. For preparative isolation of the Lbp1 and Lbp2 proteins, the washed pellets were poured into a 1 cm diameter chromatography column and the proteins were eluted by application of 2M guanidine hydrochloride.

There is considerable heterogeneity in the size of the Tbp2 protein isolated from different strains and species of bacteria. (FIG. 1, arrowhead). Although there may be some variation in size amongst the Lbp2 proteins from different species, they are much more uniform in size.

Figure 2:
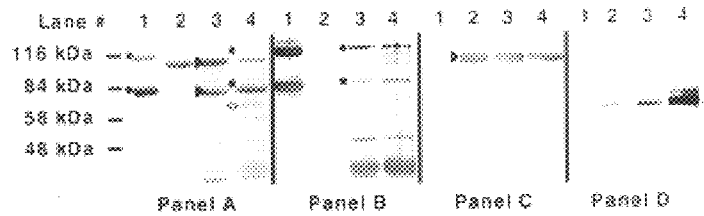
FIG. 2 shows the specific identification by immunoblot analysis of transferrin binding proteins and lactoferrin binding proteins isolated from bacterial pathogens.

To further characterize the lactoferrin receptor protein Lbp2, various sera were tested for reactivity to the protein. Following affinity isolation of Tbp1+2, Lbp1 and Lbp1+2, the samples were subjected to SDS-PAGE, and were subsequently electroblotted and analyzed for reactivity against various antisera (FIG. 2). The separated proteins were subsequently electrophoretically transferred onto Nitrocellulose membranes (Western blot). After blocking the remaining binding sites with a solution of Tris-buffered saline (TBS) containing 0.5% skim milk, the blots were incubated in the presence of rabbit polyclonal antisera (1:5000) directed towards either the affinity isolated *M. catarrhalis* Tbp1+2 proteins, Lbp1 protein, or towards human lactoferrin. In FIG. 2, Lane 1 contains transferrin receptor proteins Tbp1 and Tbp2 isolated from *M. catarrhalis*, Lane 2 contains lactoferrin receptor protein Lbp1, Lanes 3 and 4 contain mixtures comprising a first lactoferrin receptor protein having a molecular weight of about 100,000 to about 105,000 daltons (Lbp1) and a second lactoferrin receptor protein having a molecular weight of between about 70,000 and about 90,000 (Lbp2). The mixture in Lane 4 was isolated utilizing lactoferrin biotinylated via its oligosaccharide side chain (Lane 4). In FIG. 2, Panel A is stained with Coomassie brilliant blue. When tested with antisera against Tbp1 and Tbp2 (Panel B), reactive bands representing Tbp1 (asterisk) and Tbp2 (dot) were observed in the samples from the modified affinity methods (lanes 3 and 4). Although careful inspection of the results clearly indicates that these are distinct from the major bands isolated with the lactoferrin affinity resin, it is also evident that the modified affinity method results in preparations that contain numerous contaminating proteins.

Reaction of the electroblotted proteins with antiserum against Lbp1 (Panel C) confirmed that the major upper band (open arrowhead) was Lbp1. This result also demonstrated that the second band Lbp2 (closed arrowhead) was not a breakdown product of Lbp1. Antiserum prepared against human lactoferrin did not react with the second major band Lbp2 (closed arrowhead) but with a minor contaminating band that was more evident in samples obtained from the modified affinity methods (open diamond, particularly lane 4).

Although the results in FIGS. 1 and 2 clearly demonstrate that an additional protein is isolated with the modified affinity methods using lactoferrin as the ligand, they do not conclusively demonstrate that this protein Lbp2 is binding directly to lactoferrin. Therefore a purified preparation of Lbp2, as well as the other receptor proteins was obtained and binding properties evaluated. To selectively affinity purify the Lbp1 and Lbp2, the sample was processed under standard conditions for Lbp1 isolation, and allowed to incubate for 1 hour with human lactoferrin-Sepharose. After separating the resin by centrifugation, the supernatant containing the Lbp2 was diluted tenfold with 50 mM pH 6 Tris buffer, and incubated for two hours with a second aliquot of human lactoferrin-Sepharose, and processed as described above for Lbp1+2 isolation. The human lactoferrin-Sepharose-bound Lbp1 and Lbp2 were eluted using 50 mM Tris buffer, pH 8 containing 3 M Guanidine-HCl and 0.3% Sarkosyl, and dialyzed against 50 mM Tris-HCl buffer, pH 8, then lyophilized.

To selectively purify the Lbp1+2 or Lbp2 alone without contaminating Tbp 1+2 present, it was necessary to affinity isolate the Tbp1+2 from the solubilized membranes, using human transferrin-Sepharose prior to subjecting the extract to the modified affinity isolation protocol. Using this strategy purified preparations of Tbp1+2 (FIG. 3, lane 1), Lbp1 (lane 2) and Lbp2 (lane 3) were obtained. The purified preparations were immobilized on a nitrocellulose membrane and subsequently tested for binding activity in the solid-phase binding assay. The results are shown in FIG. 4 and demonstrated that, similar to Lbp1, Lbp2 specifically bound labelled human lactoferrin but not labelled human transferrin nor labelled bovine lactoferrin.

Example 5

This Example describes the specific binding of lactoferrin and transferrin by receptor proteins by a solid-phase binding assay.

The selectively eluted Tbp1+2, Lbp1 alone or Lbp2 alone were spotted onto HA-nitrocellulose paper placed into a dot blot apparatus with vacuum apparatus attached. The remaining binding sites on the blot were blocked with Tris-buffered saline containing 0.5% skim milk. The individual wells of the blot were then incubated with horse-radish peroxidase-labelled human lactoferrin (HRP-hLf), human transferrin (HRP-hTf), or bovine lactoferrin (HRP-bLf) in the presence or absence of excess unlabelled hLF or hTf.

Example 6

This Example describes the polymerase chain reaction (PCR) amplification of the *N. meningitides* P3006 lbpB C-terminal region. An open reading frame presumptively encoding a Tbp2 homologue was identified upstream of the lbpA gene in meningococcal strain H44/76 (refs. 22, 35). The target DNA to be amplified was prepared by growing an overnight liquid culture of organisms, transferring 1.5 ml to a sterile microfuge tube, centrifuging the sample, and discarding the supernatant. The cell pellet was resuspended in a small volume of sterile water, boiled for 5 minutes, centrifuged and the supernatant was used as template for subsequent PCR analysis. One primer was designed to match the known sequence of the lbpB coding region of the C-terminal portion of the H44/76 LbpB (Lbp2) (approximately the last quarter of the coding sequence), and the second primer was designed to match the region which encodes for the signal peptide region of the LbpA (Lbp1) protein. The region was amplified using chromosomal DNA from strain P3006. This strain was shown to possess a functional Lbp2 protein which could be affinity purified (FIG. 1, lane 13). Annealing temperatures used for the amplification were stringent (greater that 55° C.), and an extension time of one minute with standard extension and DNA-melting parameters (72° C. and 94° C. respectively). Commercially available Taq DNA polymerase (Bethesda Research Labs) and a Perkin Elmer DNA Thermal Cycler were used for the DNA amplification. The resulting 557 base pair PCR product was cloned directly into the vector pCRII, which allows direct cloning of PCR fragments amplified using Taq DNA polymerase. An isolate was chosen that had the PCR fragment cloned in the opposite orientation of the pCRII lac promoter region so that any potentially toxic Lbp2-fusion proteins would not be produced, and thus decreasing the likelihood of lbpb gene rearrangements. The DNA was sequenced, and the derived amino acid sequence was compared to that of known Lbp2 and Tbp2 derived amino acid sequences (Table 3). The protein has a number of regions that showed considerable homology to the Lbp2 and Tbp2 proteins of the various pathogens. Also there is a stretch of amino acids which is rich in negatively-charged residues evident in M986 and H44/76 Lbp2s (−50 to −16 and −57 to −16, respectively, Table 4) that was not present in the P3006 Lbp2.

SUMMARY OF THE DISCLOSURE

In summary of this disclosure, the present invention provides a novel lactoferrin receptor protein, which is isolated and purified from a solubilized membrane preparation from a pathogen, having a molecular weight of between about 70,000 and about 90,000 daltons, compositions comprising the same and procedures for the preparation thereof. Modifications are possible within the scope of this invention.

TABLE 1

Bacterial Species with Transferrin or Lactoferrin Receptors

| Host | Bacterial Species | Receptor | Disease | Reference |
| --- | --- | --- | --- | --- |
| Human | *Neisseria meningitides* | Tf, Lf | meningitis | 4 |
|  | *Areisseria gonorrhoeae* | Tf, Lf | gonorrhea | 5 |
|  | *Moraxella catarrhalis* | Tf, Lf | otitis media | 5 |
|  | *Moraxella lacunata* | Tf, Lf | conjunctivitis | this work |
|  | *Haemophilus influenzae* | Tf | meningitis | 6 |
| Bovine | *Moraxella bovis* | Tf, Lf | keratoconjunctivitis | 7 |
|  | *Pasteurella haemolytica* | Tf | shipping fever | 8 |

TABLE 1-continued

Bacterial Species with Transferrin or Lactoferrin Receptors

| Host | Bacterial Species | Receptor | Disease | Reference |
|---|---|---|---|---|
| | Pasteurella multocida | Tf | haemorrhagic septicemia | 9 |
| | Haemophilus somnus | Tf | TEME | 10 |
| Equine | Actinobacillus equuli | Tf | | 7 |
| Porcine | Actinobacillus pleuropneumoniae | Tf | pneumonia | 11 |
| Avian | Haemophilus paragallinarum | Tf | infectious coryza | 12 |
| | Haemophilus avium | Tf | | 12 |

TABLE 2

Utilization of Lactoferrin and Transferrin Iron for Growth

| Bacterial Strain | Growth of Bacteria utilizing the Protein Source of Iron | | | |
|---|---|---|---|---|
| | hTf | bTf | hLf | bLf |
| N. meningitidis | + | − | + | − |
| N. meningitidis 1bpA::Gm | + | − | − | − |
| N. meningitidis tbpA::Kan | − | − | + | − |
| N. catarrhalis | + | − | + | − |
| M. bovis | − | + | − | + |

+, growth surrounding the disk containing the specified iron source; −, no detectable growth

TABLE 3

Comparative Analysis of Lbp2 and Tbp2 Amino Acid Sequences

| Species | Strain | Protein | Alignment | Amino Acid Position | Alignment | Amino Acid Position | Reference |
|---|---|---|---|---|---|---|---|
| N. meningitidis | H44/76 | Lbp2 | GGFYGPQAEELGG | (−70 to −58) | VVFGAK | (−14 to −9) | 21 |
| N. meningitidis | P3006 | Lbp2 | ******A | (−37 to −25) | **** | (−14 to −9) | This work |
| N. meningitidis | M986 | Lbp2 | ******E*A**** | (−77 to −65) | ****** | (−14 to −9) | 36 |
| N. meningitidis | M982 | Tbp2 | ****K** | (−52 to −40) | **** | (−12 to −7) | 37 |
| N. meningitidis | B16B6 | Tbp2 | *****KN*I*M** | (−42 to −30) | ****** | (−12 to −7) | 37 |
| N. gonorrhoeae | FA19 | Tbp2 | ****N** | (−52 to −40) | **** | (−14 to −9) | 38 |
| R. influenzae | DL63 | Tbp2 | *A****H*T**** | (−51 to −39) | ****** | (−14 to −9) | 39 |
| A. pleuropneumoniae | H49 | Tbp2 | ****K*MA* | (−35 to −23) | A***** | (−11 to −6) | 40 |
| A. pleuropneumoniae | AP205 | Tbp2 | ****K*MA* | (−35 to −23) | A***** | (−11 to −6) | 41 |

Note:
* indicates identical amino acid. The stop signal is the "0" position. This was done since the start of the Lbp2 protein (i.e. the true number of amino acids is not yet known).

TABLE 4

Comparative Analysis of N. meningitidis H44/76, P3006 and M986 Lbp2 amino acid sequences

| Strain | Alignment | |
|---|---|---|
| H44/76 | LKGIRTAEADIPQTGKARYIGTWEARI | (−183 to −157) |
| P3006 | ****************H******* | (−161 to −135) |
| H44/76 | IQWDNHADKKAAKAEFDVDFGEKSISGTLTEKNGVQPAFHIENGVIEGNGFHATARTRDNG | (−153 to −93) |
| P3006 | KY*-NQG***Q*T**ALK*DTH*YK*D****LE | (−119 to −60) |
| H44/76 | STNPPSFKANNLLVT | (−85 to −71) |
| P3006 | **QS**G | (−53 to −39) |
| H44/76 | GGFYGPQAEELGGTIFNNDGKSLGITEDTENEAEAEVENEAGVG-------EQLKPEAKPQFGVVFGAKKDNKEVEK* | (−70 to 0) |

TABLE 4-continued

Comparative Analysis of N. meningitidis H44/76, P3006 and M986 Lbp2 amino acid sequences Strain Alignment

```
P3006    ********A****N*IDS*R*I------------------------------------********MQ*****      (-37 to 0)
M986     ******E******I*************G***KV**D*DVDVD*DVDADADV*****V******************   (-77 to 0)
```

Note:
* indicates identical amino acid.
- indicates gaps in the amino acid alignment.
The stop codon is the "0" position, since the entire Lbp2 sequence is not yet known. The M986 Lbp2 sequence was not included in all alignments since only limited Lbp2 amino acid sequence was available. In addition, the M986 lbpb sequence was changed from the original published sequence to add a G at position 1, and a C at position 15. This allows for a presumed correct reading frame of the lbpB gene and encodes for the highly conserved GGFYG.

REFERENCES

1. Guerinot, M. L. (1994) Microbial iron transport. *Annu Rev Microbial* 48: 743–772.
2. Crosa, J. H. (1989) Genetics and molecular biology of siderophore-mediated iron transport in bacteria. *Microbial Lett* 53: 517–530.
3. Schryvers, A. B. and Gonzalez, G. C. (1990) Receptors for transferrin in pathogenic bacteria are specific for the host's protein. *Can J Microbiol* 36: 145–147.
4. Schryvers A. B. and Morris, L. J. (1988a) Identification and characterization of the transferrin receptor from *Neisseria meningitidis*. *Mol Microbiol* 2: 281–288.
5. Schryvers, A. B. and Lee, B. C. (1989) Comparative analysis of the transferrin and lactoferrin binding proteins in the family Neisseriaceae. *Can J Microbial* 35: 409–415.
6. Schryvers A. B. and Gray-Owen, S. (1992) Iron acquisition in *Haemophilus influenzae*: Receptors for human transferrin. *J Infect Dis* 165 Suppl. 1: S103–S104.
7. Yu, R.-H, Gray-Owen, S. D., Ogunnariwo, J., and Schyrvers, A. B. (1992) Interaction of ruminant transferrin receptors in bovine isolates of *Pasteurella haemolytica* and *Haemophilus somnus*. *Infect Immun*. 60: 2992–2994.
8. Ogunnariwo, J. A. and Schryvers, A. B. (1990) Iron acquisition in *Pasteurella haemolytica*: Expression and identification of a bovine-specific transferrin receptor. *Infect Immun* 58: 2091–2097.
9. Ogunnariwo, J. A., Alcantara J., and Schryvers, A. B. (1991) Evidence for non-siderophore-mediated acquisition of transferrin-bound iron by *Pasteurella multocida*. *Microbial Pathogenesis* 11: 47–56.
10. Ogunnariwo, J. A., Cheng, C. Y., Ford, J. A., and Schryvers, A. B. (1990) Response of *Haemophilus somnus* to iron limitation: Expression and identification of a bovine-specific transferrin receptor. *Microbial Pathogenesis* 9: 397–406.
11. Gonzalez, G. C., Caamano, D. L., and Schryvers, A-B. (1990) Identification and characterization of a porcine-specific transferrin receptor in *Actinobacillus pleuropneumoniae*. *Mol Microbial:* 4: 1173–1179.
12. Ogunnariwo, J. A. and Schryvers, A. B. (1992), Correlation between the ability of *Haemophilus paragallinarum* to acquire ovotransferrin-bound iron and the expression of ovotransferrin-specific receptors. *Avian Dis* 36: 655–663.
13. Legrain, M., Jacobs, E., Irwin, S. W., Schryvers, A-B., and Quentin-Millet, M. J. (1993) Molecular cloning and characterization of *Neisseria meningitidis* genes encoding the transferrin binding proteins Tbp1 and Tbp2. *Gene* 130: 73–80.
14. Anderson, J. A.,. Sparling, P. F., and Cornelissen, C. N. (1994) Gonococcal transferrin-binding protein 2 facilitates but is not essential for transferrin utilization. *J. Bacterial* 176: 3162–3170.
15. Cornelissen, C. N., Biswas, G. D., Tsai, J., Paruchuri, D. K., Thompson, S. A., and Sparling, P. F. (1992) Gonococcal transferrin-binding protein 1 is required for transferrin utilization and is homologous to TonB-dependant outer membrane receptors. *J Bacteriol* 174: 5788–5797.
16. Gray-Owen, S. D., Loosmore, S., and Schryvers, A. B. (1995) Identification and characterization of genes encoding the human transferrin binding proteins from *Haemophilus influenzae*. *Infect Immun* (In Press).
17. Gonzalez, G. C., Yu, R-H., Rosteck, P., and Schryvers, A-B. (1995) Characterization of the *Actinbacillus pleuropneumoniae* transferrin receptor genes and their products. *Microbial* (manuscript submitted).
18. Gerlach, G. F., Anderson, C., Potter, A. A., Klashinsky, S., and Willson, P. J. (1992a) Cloning and expression of a transferrin-binding protein from *Actinobacillus Pleuropneumoniae*. *Infect Immun* 60: 892–898.
19. Gerlach, G. F., Klashinsky, S., Anderson, C., Potter, A. A., and Willson, P. J. (1992b) Characterization of two genes encoding distinct transferrin-binding proteins in different *Actinobacillus pleuropneumoniae* isolates. *Infect Immun* 60: 3253–3261.
20. Ala'Aldeen DAA, Powell NBL, Wall RA, Borfiello SP. Localization of the meningococcal receptors for human transferrin. *Infect Immun* (1993), 61-751–759.
21. Irwin, S. W., The Role of the Transferrin Binding Proteins of *Neisseria meningitidis* in Iron Acquisition from Human Transferrin. (1994), Ph.D. Thesis, University of Calgary, Calgary.
22. Irwin, S. W., Auerill, N., Chang T-Y., Preparation and analysis of Isogenic Mutants in the Transferrin Receptor Protein Genes, Tbp1, Tbp2 from *Neisseria meningitidis*, Mol. Microbiol. Vol. 8: 1125–1135 (1993).
23. Murphy CK, Kalve VI, Klebba PE. Surface topology of the *Escherichia coli* K-12 ferric enterobactin receptor. *J Bacteriol* (1990), 172: 2736–2746.
24. Petersson, A, Maas, A, and Tommassen, J. (1994) Identification of the iroa gene product of *Neisseria meningitidis* as a lactoferrin receptor. *J Bacterial* 176: 1764–1766.
25. Rutz, J. M., Lui J., Lyons, J. A, Goranson, J., Armstrong, S. K., McIntosh, M. A., Feix, J. B., and Klebba, P. E. (1992) Formation of gated channel by a ligand-specific transport protein in the bacterial outer membrane. *Science* 258: 471–475.
26. Petersson, A, Van der Ley, P., Poolman, J. T., and Tommassen, J. (1993) Molecular characterization of the 98-kilodalton iron-regulated outer membrane protein of *Neisseria meningitidis*. *Infect Immun* 61: 4724–4733.

27. Kirby SD, Ogunnariwo JA, Schryvers AP. Receptor-mediated iron acquisition from transferrin in the Pasteurellaceae. In: Donachie W, Hodgson R, Lainson A. eds. Haemophilus, Actinobacillus and Pasteurella. London: Plenum Publishing Co. (1995), 28. Quinn ML, Weyer SJ, Lewis LA, Dyer DW, Wagner PM. Insertional inactivation of the gene for the meningococcal lactoferrin binding protein. *Microb Pathog* 1994, 17:227–237.

29. Lockhoff, O. Glycolipids as Immunomodulators: Synthesis and Properties. 1991. Chem. Int. Ed. Engl. 30:1611–1620.

30. Nixon-George et al (1990), J. Immunology, 144:4798–4802.

31. Yu R-H, Schryvers AB. The interaction between human transferrin and transferrin binding protein 2 from *Moraxella (Branhamella) catarrhalis* differs from that of other human pathogens. Microbial Pathogenesis 1993; 15: 443–445.

32. Yu R-H, Schryvers AB. Transferrin receptors on ruminant pathogens vary in their interaction with the C-lobe and N-lobe of ruminant transferring. *Can J. Microbiol* (1994); 40: 532–540.

33. Schryvers AB, Morris LJ. Identification and characterization of the human lactoferrin-binding protein from *Neisseria meningitidis*. *Infect Immun* 1988; 56: 1144–1149.

34. Ogunnariwo JA, Schryvers AB. Iron acquisition in *Pasteurella haemolytica*: Expression and identification of a bovine-specific transferrin receptor. *Infect Immun* (1990); 58: 2091–2097.

35. Pettersson A, Klarenbeek V, van Deurzen J, Poolman JT, Tommassen J., Molecular characterization of the structural gene for the lactoferrin receptor of the meningococcal strain H44/76. *Microbial Pathogenesis* 1994, 17: 395–408.

36. Pettersson A, Van der Ley P, Poolman JT, Tommassen J. Molecular characterization of the 98-kilodalton iron-regulated outer membrane protein of *Neisseria meningitides*. *Infect Immun* (1993), 61: 4724–4733.

37. Legrain M, Jacobs E, Irwin SW, Schryvers AB, Quentin-Millet MJ. Molecular cloning and characterization of *Neisseria meningitidis* genes encoding the transferrin binding proteins Tbp1 and Tbp2. *Gene* (1993), 130: 73–80.

38. Anderson JA, Sparling PF, Cornelissen CN. Gonococcal transferrin-binding protein 2 facilitates but is not essential for transferrin utilization. *J Bacteriol* (1994) 176: 3162–3170.

39. Gray-Owen SD, Loosemore S, Schryvers AB. Identification and characterization of genes encoding the human transferrin binding proteins from *Haemophilus influenzae.*, *Infect Immun* (1995), 63: 1201–1210.

40. Gonzalez GC, Yu R-H, Rosteck P, Schryvers AB, Characterization of the *Actinobacillus pleuropneumoniae* transferrin receptor genes and their products. *Microbiol* 1995, (In Press)

41. Gerlach GF, Anderson C, Potter AA, Klashinsky S, Willson PJ. Cloning and expression of a transferrin-binding protein from *Actinobacillus pleuropneumoniae*. *Infect Immun* (1992), 60: 892–898.

What we claim is:

1. A method of producing a lactoferrin receptor protein from a bacterial pathogen selected from the group consisting of *Neisseria meningitdis, Neisseria gonorrhoeae, Moraxella catarrhalis, Moraxella bovis* and *Moraxella lacunata*, comprising the steps of:

(a) providing a solubilized membrane preparation from said bacterial pathogen containing lactoferrin receptor proteins, transferrin receptor proteins and other contaminants, said lactoferrin receptor proteins being a first lactoferrin receptor protein having a molecular weight of 100,000 to 105,000 daltons, as determined by sodium dodecyl sulphate polyacrylamide gel electrophoresis (SDS-PAGE), and a second lactoferrin receptor protein having a molecular weight of between 70,000 and 90,000 daltons, as determined by SDS-PAGE, (b) complexing both said first and second lactoferrin receptor proteins with lactoferrin and purifying the resulting complexes free from said transferrin receptor proteins and said other contaminants to provide purified complexes, and (c) separating from the purified complexes both said first and second lactoferrin receptor proteins in the form of a mixture.

2. A method of producing a lactoferrin receptor protein from a bacterial pathogen selected from the group consisting of *Neisseria menngitidis, Neisseria aonorrhoeae, Moraxella catarrhalis, Moraxella bovis* and *Moraxella lacunata*, which comprises the steps of:

(a) providing a membrane preparation from the bacterial pathogen, (b) solubilizing the membrane preparation to form a solubilized membrane preparation containing a selected lactoferrin receptor protein, transferrin receptor protein and other contaminants, wherein said selected lactoferrin receptor protein has a molecular weight of 100,000 to 105,000 daltons, as determined by SDS-PAGE (c) complexing said selected lactoferrin receptor protein with lactoferrin and complexing said transferrin receptor protein with transferrin and purifying the resulting lactoferrin- and transferrin-complexes free from each other and said other contaminants to provide a first purified lactoferrin complex and purified transferrin complex, thereby removing said selected lactoferrin receptor protein and said transferrin receptor proteins from said solubilized membrane preparation to provide a depleted membrane preparation, (d) solubilizing said depleted membrane preparation to form a solubilized membrane preparation containing a second lactoferrin receptor protein having a molecular weight of between 70,000 and 90,000 daltons, as determined by SDS-PAGE, (e) complexing said second lactoferrin receptor protein with lactoferrin and removing the complex so formed from said depleted membrane preparation to provide second lactoferrin complexes, (f) separating from the first lactoferrin complexes said selected lactoferrin receptor protein, and (g) separating from the second lactoferrin complexes said second lactoferrin receptor protein.

3. The method of claim 1 or 2 wherein said lactoferrin is coupled to a carrier molecule.

4. The method of claim 3 wherein the carrier molecule is Sepharose.

5. The method of claim 4 wherein the Sepharose is cyanogen bromide activated CH-Sepharose.

6. The method of claim 4 wherein the lactoferrin is conjugated to biotin and the Sepharose is streptavidin-Sepharose to couple the lactoferrin to the Sepharose.

* * * * *